United States Patent [19]
Mc Culloch et al.

[11] Patent Number: 5,889,180
[45] Date of Patent: Mar. 30, 1999

[54] USE OF SMALL PORE SILICAS AS A SUPPORT FOR A CHIRAL STATIONARY PHASE

[75] Inventors: Beth Mc Culloch, Clarendon Hills; Peter K. Nickl, Des Plains; Timothy A. Brandvold, Buffalo Grove, all of Ill.

[73] Assignee: UOP LLC, Des Plaines, Ill.

[21] Appl. No.: 966,740

[22] Filed: Nov. 10, 1997

[51] Int. Cl.$^6$ ............................. B01D 15/08; C07H 1/06
[52] U.S. Cl. ........................ 536/127; 210/656; 536/56; 536/58; 536/112; 536/123.1; 536/123.12; 536/124
[58] Field of Search ................ 536/58, 56, 112, 536/123.1, 123.12, 124, 127; 210/656, 660

[56] References Cited

U.S. PATENT DOCUMENTS

| | | | |
|---|---|---|---|
| 4,818,394 | 4/1989 | Okamoto et al. | 210/198.2 |
| 4,861,872 | 8/1989 | Okamoto et al. | 536/18.7 |
| 5,066,793 | 11/1991 | Francotte et al. | 536/50 |
| 5,354,852 | 10/1994 | Ikeda | 536/17.9 |
| 5,496,937 | 3/1996 | Okamoto et al. | 536/124 |
| 5,518,625 | 5/1996 | Priegnitz et al. | 210/659 |
| 5,543,506 | 8/1996 | Okamoto | 536/18.7 |
| 5,589,061 | 12/1996 | Russell | 210/198.2 |
| 5,639,824 | 6/1997 | Okamoto | 525/54.2 |
| 5,641,404 | 6/1997 | Nicholson et al. | 210/635 |
| 5,656,158 | 8/1997 | Russell | 210/198.2 |
| 5,663,311 | 9/1997 | Okamoto | 536/18.7 |
| 5,679,572 | 10/1997 | Okamoto et al. | 435/803 |

OTHER PUBLICATIONS

*Application Guide for chiral column selection*, published by Chiral Technologies, Inc., pp. 86–95, (1995).

Ichida, Akito. *Bunseki Kagaku*, vol. 46(8):613–625, (1997). Abstract Only.

Grieb et al. *Chirality*, vol. 6(2):129–134, (1994). Abstract Only.

Gattuso et al. *S.T.P Pharma Prat.*, vol. 7(1):50–55, (1997). Abstract Only.

Gattuso et al. *Chem. Tech. Eur.*, vol. 3(3):27–30, (1996).

*Primary Examiner*—Howard C. Lee
*Attorney, Agent, or Firm*—Thomas K. McBride; Frank S. Molinaro

[57] ABSTRACT

Small pore silicas serving as the inert core support in chiral stationary phases show a surprising increase in column capacity relative to conventional chiral stationary phases having large pore silicas as the inert core support. This affords increased productivity and lower overall costs for chiral resolutions using a chiral stationary phase as adsorbent and an achiral liquid as eluant.

9 Claims, No Drawings

USE OF SMALL PORE SILICAS AS A SUPPORT FOR A CHIRAL STATIONARY PHASE

BACKGROUND OF THE INVENTION

Recently, chromatographic separation of enantiomers from their racemic mixture using a chiral stationary phase has received considerable attention, arising in large part from the availability of relatively inexpensive chiral stationary phases. The stationary phase generally consists of a chiral organic moiety, as for example cellulosic materials, attached to an underlying inert core support such as silica. It was believed that large pore silicas (e.g., pore sizes larger than about 500 angstroms) were necessary for an efficient and effective chiral stationary phase, and in fact, silicas with a pore size greater than about 1000 angstroms have been favored as the inert core support. To our surprise, we have found small pore silicas, i.e., silicas with a mean pore size less than about 100 angstroms, to be quite effective in separation of enantiomers using a chiral stationary phase using simulated moving bed chromatography. Although Grieb et al., *Chirality*, 6, 129 (1994) recently have shown that silicas of 120 angstrom pore size can function well in analytical columns we have observed some quite unanticipated properties which make even smaller-pore size silicas (50–100 angstrom pore size) still more desirable for use in simulated moving bed chromatography.

To better understand our invention in the context of theory and conventional practice it will be helpful to briefly review some of the principles of liquid chromatography most relevant to our invention. One fundamental property in liquid chromatography is k', the capacity factor, which is defined as $$k' = n_s/n_m \tag{1}$$

where $n_s$ is the total moles of material being separated in the stationary phase and $n_m$ is the number of moles of this material in the mobile phase. Where there are several components present, the capacity factor for the ith component is $$k'(i) = n_s(i)/n_m(i)$$

It is clear from this expression that the larger is k' the greater will be the capability of the stationary phase to absorb the component, but also the larger will be the amount of solvent to totally desorb it.

The retention time, $t_r$, for component i, $t_r(i)$, is related to the time it takes for the mobile phase to travel the length of the column, $t_0$, by the distribution of component between the stationary and mobile phases according to the equation, $$t_r(i) = \frac{t_0}{\frac{n_m(i)}{n_m(i) + n_s(i)}} = t_0 \frac{[n_m(i) + n_s(i)]}{n_m(i)} \tag{2}$$

$$t_r(i) = t_0[1 + k'(i)]$$

Rearranging, $$k'(i) = \frac{t_r(i) - t_0(i)}{t_0(i)}$$

Thus, the capacity factor k' also is related to the relative retention time of the components in question.

For two components, the ratio of their relative retention times, α, is $$\alpha_{ij} = \frac{t_r(i) - t_0}{t_r(j) - t_0} = \frac{k'(i)}{k'(j)}$$

where $\alpha_{ij}$ is the selectivity factor between components i and j. In traditional analytical chromatography one desires to maximize the selectivity so as to effect complete separation of the components. Finally, the volume, $V_r$, of the mobile phase required to elute a component as measured to the apex of the peak is related to the flow rate, F, of the mobile phase and retention time of the component by, $$V_r(i) = t_r(i)F$$

from which it follows that $$V_r(i) = V_0[1 + k'(i)] \tag{4}$$

$$[V_r(i) - V_0]/V_0 = k' \tag{5}$$

and $$\frac{V_r(i) - V_0}{V_r(j) - V_0} = \frac{t_r(i) - t_0}{t_r(j) - t_0} = \frac{k'(i)}{k'(j)} = \alpha_{ij} \tag{6}$$

Thus, classical liquid chromatography theory as supported by much experimental evidence leads to the conclusions that the retention volume of a particular component, relative to the retention volume of the pure mobile phase, depends only on the capacity factor for the component, although relative retention volumes and relative retention times for two components depend only on the ratio of the two capacity factors, and it is the ratio of the capacity factors which define selectivity.

One form of chromatography well adapted to continuous, commercial-size separation is simulated moving bed chromatography. In continuous moving bed chromatography the stationary phase moves relative to the feed and mobile phase inputs, and the extract and raffinate outputs. Because of the difficulty of implementing a moving stationary phase in chromatographic separations its simulation is favored in practice (hence the name simulated moving bed chromatography) where incremental positional changes of the input and output streams, relative to a static stationary phase, is effected at regular intervals. Although many of the foregoing relations apply to simulated moving bed chromatography some additional nuances are applicable when the separations are of chiral substances using conventional chiral stationary phases.

The conditions in simulated moving bed chromatography can be significantly modified from those required for analytical and batch mode preparative chromatography. In particular, the separation of enantiomers from their racemic mixture using a chiral stationary phase in simulated moving bed chromatography can be performed effectively at low values of k' (low capacity factor), thereby minimizing the amount of mobile phase which is needed. Since an appreciable cost of the separation process is associated with the mobile phase and its recovery from the raffinate and extract streams, operation at a low capacity factor affords substantial cost savings accruing from a lower mobile phase inventory, lower utility costs in recovering the mobile phase, and other ancillary costs. But inquiry does not end here!

Recently we have evaluated the effects of several chromatographic variables on the cost of effecting chiral separations by simulated moving bed chromatography. One result is that separation costs decrease with an increase in the capacity factor, i.e., k'. For a series of materials tested under identical conditions the magnitude of the capacity factor, k', is an indication of the capacity of the stationary phase. At first this may appear counterintuitive, since increasing k' translates to increased amounts of mobile phase needed to desorb the component, and attending increases in solvent recovery costs. However, larger values of k' permit adjustments of other variables which ultimately lead to lower costs. The essential feature to focus on is that operational costs of chiral separations via SMB decrease with increasing k', a conclusion which is not apparent and may well be unexpected.

The so-called "breakthrough test" is a measure of the column capacity of a stationary phase. In a breakthrough test a feed of a specified concentration is passed over the stationary phase and the effluent is collected and analyzed. The relative concentration of each component in the effluent is plotted relative to the effluent volume and the appearance of each component is a measure of the column capacity of the stationary phase.

Our invention arises from the totally unexpected observation that as the pore size of silica is varied the capacity factor varies inversely with pore size. That is, as the silica pore size decreases, the capacity factor, k', of the chiral stationary phase for which silica is used as an inert core support increases. This, too, is counterintuitive, for the chiral organic moiety generally has a high molecular weight and would not be expected to utilize the small pores of the silicas of our invention. Nonetheless, the experimental observations are unequivocal and unassailable; chiral stationary phases having small pore silicas as an inert core support demonstrate higher capacities than analogous chiral stationary phases with large-pore silicas as the inert core support.

According to its definition, the capacity factor also is a measure of the quantity of material which the adsorbent can hold, and in SMB this is related to the capacity of the column. Column capacity is related to both the productivity of the SMB process as well as the number of active sites of any adsorbent. In general, the higher the productivity of an adsorbent, the less solvent is used, and the less solvent recovery is needed. To our surprise, we found an increase in column capacity in going from the conventional large pore silicas previously used to the 50–100 angstrom silicas of this invention. Consequently, use of such small-pore silicas as the support in CSPs for SMB chiral separations provides unexpected benefits over the use of traditional large-pore silicas, and therein lies our invention.

SUMMARY OF THE INVENTION

The purpose of our invention is to prepare a chiral stationary phase using small-pore size silica as the underlying core support. An embodiment comprises using silica with a pore size in the range between about 50 and about 100 angstroms. More specifically, the chiral stationary phases of this invention are silicas having a pore size in the range 50–100 angstroms coated with a cellulose derivative, especially a cellulose carbamate or cellulose ester. Other purposes and embodiments will be clear from the ensuing description.

DESCRIPTION OF THE INVENTION

This invention relates to a chiral stationary phase (CSP) particularly suited for separations utilizing simulated moving bed chromatography, where the underlying core support is a small pore silica. More particularly, our invention relates to chiral stationary phases where the core support of silica has an average pore size between about 50 and about 100 angstroms. The resulting CSPs are especially suited to chiral separations via simulated moving bed chromatography, since the column capacity of the CSPs of our invention are greater than those of conventional CSPs based on large-pore silicas. This result is surprising but gratifying since it affords higher productivity with lower solvent usage.

Chromatographic processes, especially liquid chromatography, appear to offer the best prospects for chiral separations. One variant of the latter utilizes achiral eluants in combination with a chiral stationary phase, which has the critical aspect that a variety of chiral stationary phases be available to the practitioner. In recent years substantial progress has been made by developing a class of chiral stationary phases based upon derivatized polysaccharides, especially cellulose, adsorbed on a carrier or support. This recently has been summarized by Y. Okamoto, *J. Chromatog.*, 666 (1994) 403–19.

Although this class of chiral stationary phase shows excellent stability for an adsorbed chiral organic material, nonetheless gradual dissolution of the chiral organic material does occur. Thus, one limitation of the prior art, polysaccharide chiral stationary phases, is that the chiral component is merely adsorbed on the carrier, which has the unavoidable consequence that the stationary phase itself may leach with appropriate solvents. The practical consequence of the chiral stationary phase bound solely by adsorption is to limit the range of solvents which may be used as eluants in the chromatographic resolution of racemates. This is an undesirable restriction which limits not only the flexibility of chromatography-based optical resolution but also substantially increases its cost through the gradual loss of expensive chiral stationary phase. Thus the need for a more "permanent" chiral stationary phase has been recognized and solutions for polysaccharide-based systems designed on a covalent tether anchoring the chiral stationary phase to the carrier has been disclosed. Y. Okamoto, et al., *J. Liq. Chromatog.*, 10 (1987), 1613–28; U.S. Pat. No. 4,619,970.

Our invention is intended to encompass chiral stationary phases having a chiral organic material merely adsorbed on its surface, as well as having a chiral organic material which is covalently bonded, however indirectly, to the underlying support. However, because the underlying support properties may be more important in those cases where the chiral organic material is merely adsorbed on the support, we place greater emphasis on this aspect of the invention.

Since the chiral organic materials used in chiral stationary phases are well known in the prior art, a detailed discussion and description is not necessary here. However, we note that chiral organic materials which are esters and carbamates of polysaccharides are of particular importance in the practice of our invention, if only because of the practicality of using them as the chiral material. Within this class, cellulose esters and carbamates are by far the most important. Analogous derivatives of amylose, chitosan, xylan, dextran, and inulin are representative of other polysaccharides which have been so used.

The chiral organic material is adsorbed on the silica support, usually by contacting the silica with a suitable solution of the chiral organic material, for example, the polysaccharide ester or carbamate. The support can be "passivated" by prior treatment with a suitable silane. This aspect of the procedure is well documented and need not be reviewed in any detail at this time; see, for example, Okamoto, et al., U.S. Pat. No. 4,818,394, for a representative procedure. However, it needs to be noted that passivation by treatment with a silane, such as 3-aminopropyltriethoxysilane and octadecyltriethoxysilane, is preferred in the practice of our invention.

The following examples merely illustrate our invention and are not intended to limit it in any way.

EXAMPLES

Preparation of Chiral Stationary Phases. Three 40 micron silica materials were obtained from Amicon. The pore sizes were 70 Å, 100 Å and 1,000 Å and all three materials were bonded with aminopropylsilane. The materials were coated with cellulose tris-(3,5-dimethylphenylcarbamate) using identical procedures and then slurry packed into columns with dimensions of 1 cm ID by 25 cm length.

Microcrystalline cellulose (Baker, 7.5 grams) was slurried with 85 mL of pyridine under a nitrogen atmosphere in a 250 mL flask fitted with overhead stirrer, thermowell, and Dean-Stark trap/reflux condenser. The mixture was heated to reflux (~104° C.) for one hour with stirring, and approximately 15 mL of overhead vapor that condenses into the D-S trap was drained and discarded. The mixture was allowed to cool to less than 40° C. The Dean-Stark trap was removed and a dry pressure-equalizing addition funnel was installed to the reaction set-up. A solution of 25.0 grams of 3,5-dimethylphenylisocyanate (0.17 mol) in 30 mL of pyridine was prepared and charged to the addition funnel. The reaction mixture was heated again to approximately 90°–95° C. and the isocyanate solution was added to the cellulose slurry dropwise over 2 hours. The addition funnel was rinsed with 5 mL of pyridine and the rinsings were added to the reaction mixture. After the addition is complete the reaction mixture was stirred for an additional 18 hours. The reaction mixture, a dark amber viscous, mostly homogeneous liquid, was cooled to room temperature. The product was poured into 350 mL of vigorously stirred methanol, the reaction flask was rinsed with an additional 150 mL of methanol and the combined methanol fractions were stirred for 1 hour. The resulting white solid was collected by vacuum filtration and rinsed with 250 mL of methanol and 250 mL of hexane. The product was dried in air, then under vacuum to a constant weight.

Four grams of 3,5-Dimethylphenycarbamoyl cellulose was combined with 65 mL HPLC grade (no inhibitors) THF in a round-bottomed flask equipped with a magnetic stirrer and stirred until the DMPCC was dissolved. One half of this mixture was removed from the flask. 16 g of aminopropyl-silylated silica (dried at 120° C. for 2 hours under vacuum) was added to the flask and stirred for 3 hours. The majority of the THF was removed by rotary evaporation. The remaining DMPCC/THF mixture was added to the flask and stirred for 1 hour. The THF was again removed by rotary evaporation, but this process was interrupted several times to break up any large clumps with a spatula. The flask contents were not taken to complete dryness. The DMPCC coated silica was then gently ground using a mortar and pestle in an effort to separate the spherical silica particles without breaking them up. The coated silica was then dried under vacuum at ambient temperature overnight.

The properties of the materials are summarized below. As expected, the small pore material contains a higher level of aminopropylsilane due to the higher surface area. The amount of cellulose on all three materials is comparable, corresponding to about 13% carbon.

TABLE 1

Properties of Chiral Stationary Phases

| Silica | CHN (as received) | CHN (after coating) |
|---|---|---|
| Matrex APS, 1,000Å | <0.5; <0.5; <0.5 | 13.3; 1.5; 1.4 |
| Matrex APS, 100Å | 2.5; 1.0; 0.9 | 15.8; 2.4; 2.1 |
| Matrex APS, 70Å | 4.8; 1.8; 1.5 | 17.7; 3.0; 2.7 |

Chiral Resolutions. The CSP's were screened with a variety of racemates and with a mobile phase consisting of 90/10 vol-% hexane/IPA. The results with [2,2,2-trifluoro-1-(9-anthryl)ethanol] (9-MAC) are shown in Table 2. The performance of the 1,000 Å material compares favorably to that of Chiralcel® OD, having 50 μm particles and column dimensions of 1 cm ID by 25 cm length, a product of Daicel Corp. The capacity factor for the small pore materials is significantly higher than that for the large pore material.

With the 100 Å pore material, the selectivities are slightly lower but the capacity factors have almost doubled. With the 70 Å material, the selectivity declines further whereas the capacity factors increase.

TABLE 2

Summary of HPLC Results with 9-MAC

| Material | k' R(−) | k' S(+) | Alpha selectivity |
|---|---|---|---|
| Chiralcel ® OD | 2.22 | 6.76 | 3.05 |
| 1,000Å | 2.26 | 7.25 | 3.2 |
| 100Å | 5*50 | 11.74 | 2.13 |
| 70Å | 8.64 | 15.50 | 1.79 |

The performance with trans-stilbene oxide is shown below. Once again, with the small pore materials the capacities are higher and the selectivities are slightly lower. The magnitude of the capacity factor increase is less for trans-stilbene oxide than that observed with 9-MAC.

TABLE 3

Summary of HPLC Results with trans-Stilbene Oxide

| Material | k' R(−) | k' S(+) | Alpha (selectivity) |
|---|---|---|---|
| Chiraicel OD | 0.83 | 2.04 | 2.45 |
| 1000Å | 0.86 | 2.05 | 2.38 |
| 100Å | 1.17 | 2.54 | 2.17 |
| 70Å | 1.52 | 2.72 | 1.79 |

The performance with the basic compound propranolol is shown below. As observed previously, the capacity factor increases significantly with the small pore size materials and the selectivity decreases slightly.

TABLE 4

Summary ot HPLC Results with Propranolol

| Material | k' R(−) | k' S(+) | Alpha (selectivity) |
|---|---|---|---|
| Chiralcel ® OD | 3.63 | 8.03 | 2.21 |
| 1000Å | 3.94 | 8.48 | 2.15 |
| 100Å | 9.59 | 14.91 | 1.55 |
| 70Å | 16.15 | 24.40 | 1.51 |

With 3-chloro-1-phenylpropanol as the racemate the capacity factor is higher with the small pore material and the selectivity is lower.

TABLE 5

Summary of HPLC Results with CPP

| Material | k' R(−) | k' S(+) | Alpha (selectivity) |
|---|---|---|---|
| Chiralcel OD | 1.32 | 1.72 | 1.31 |
| 1000Å | 1.46 | 1.90 | 1.30 |
| 100Å | 2.77 | NA | |
| 70Å | 4.21 | NA | |

In all cases described above, the 1,000 A material has a comparable performance to that observed for Chiralcel® OD as obtained from the Daicel Corp. In fact, the agreement is surprisingly good. In all cases, the small pore materials have a higher capacity factor and a slightly lower selectivity than the large pore material. The magnitude of the capacity factor increase varies among the racemates tested. For separations on a large scale, both the capacity factor and column capacity are important parameters and their increase significantly reduces the separation costs.

Column Capacity from Breakthrough Tests. The breakthrough results were obtained in the following way. The column was equilibrated with 7–10 column volumes of mobile phase (90/10 hexane/IPA) at a flow rate of 4.7 mL/min. A feed composing of 0.5 wt. % 1,3,5-tri-(t-butyl) benzene (tracer) and 1 wt. % trans-stilbene oxide (0.5 wt. % of each enantiomer) was prepared in mobile phase. The feed solution was passed over the column for 15 minutes (adsorption cycle) and fractions were collected in a fraction collector. After 15 minutes, mobile phase was introduced (desorption cycle) and fractions were collected. The fractions were analyzed on an analytical column and the relative concentration of each component was expressed relative to the retention volume. The results of the breakthrough tests are summarized in Table 6.

TABLE 6

Summary of Breakthrough Tests Results
Obtained with trans-Stilbene Oxide

| Material | Total Capacity[a] | Cap. R(−)[a] | Cap. S(+)[a] |
|---|---|---|---|
| 1000Å | 0.12 | 0.054 | 0.066 |
| 100Å | 0.15 | 0.057 | 0.093 |
| 70Å | 0.20 | 0.077 | 0.125 |

[a]Capacity is given in units of cc per unit column volume.

The results indicate that as the pore size decreases, the column capacity increases. These results are consistent with those obtained above.

We claim as our invention:

1. In the separation of chiral materials by simulated moving bed chromatography using a chiral stationary phase having silica as an inert core support and an achiral eluant, the improvement comprising using a chiral stationary phase in which the silica has a pore size between about 50 and about 100 angstroms.

2. A process for the separation of at least one chiral substance from a mixture of chiral substances comprising adsorbing said chiral substance on a chiral stationary phase and eluting the adsorbed chiral substance using an achiral solvent, where said chiral stationary phase comprises an inert core support of silica with a pore size from about 50 up to about 100 angstroms and a chiral organic coating on said inert core support.

3. The process of claim 2 where the chiral organic coating is selected from the group consisting of polysaccharide esters and carbamates.

4. The process of claim 3 where the polysaccharide esters and carbamates are cellulose esters and carbamates.

5. The process of claim 3 where the polysaccharide esters and carbamates are selected from the group consisting of esters and carbamates of amylose, chitosan, xylan, dextran and inulin.

6. A process for the separation of at least one chiral substance from a mixture of chiral substances comprising adsorbing said chiral substance on a chiral stationary phase and eluting the adsorbed chiral substance using an achiral solvent, where said chiral stationary phase comprises an inert core support of silica with a pore size from about 50 up to about 100 angstroms and a chiral organic material covalently bonded to said inert core support.

7. The process of claim 6 where the chiral organic material is selected from the group consisting of polysaccharide esters and carbamates.

8. The process of claim 7 where the polysaccharide esters and carbamates are cellulose esters and carbamates.

9. The process of claim 7 where the polysaccharide esters and carbamates are selected from the group consisting of esters and carbamates of amylose, chitosan, xylan, dextran, and inulin.

* * * * *